United States Patent
Barnard et al.

(10) Patent No.: US 6,406,431 B1
(45) Date of Patent: Jun. 18, 2002

(54) SYSTEM FOR IMAGING THE BLADDER DURING VOIDING

(75) Inventors: William L. Barnard, Redmond; Andrew Lundberg, Kirkland; Gerald J. McMorrow, Duvall, all of WA (US)

(73) Assignee: Diagnostic Ultasound Corporation, Bothell, WA (US)

( * ) Notice: Subject to any disclaimer, the term of this patent is extended or adjusted under 35 U.S.C. 154(b) by 0 days.

(21) Appl. No.: 09/506,416

(22) Filed: Feb. 17, 2000

(51) Int. Cl.[7] ................................................. A61B 8/00
(52) U.S. Cl. ...................................................... 600/443
(58) Field of Search ................................ 600/443, 447, 600/449, 586; 128/916

(56) References Cited

U.S. PATENT DOCUMENTS

| | | | | |
|---|---|---|---|---|
| 4,852,578 A | * | 8/1989 | Companion et al. | 600/449 |
| 4,926,871 A | * | 5/1990 | Ganguly et al. | 600/449 |
| 5,058,591 A | * | 10/1991 | Companion et al. | 600/449 |
| 5,235,985 A | * | 8/1993 | McMorrow et al. | 128/916 |
| 5,538,004 A | * | 7/1996 | Bamber | 128/916 |
| 6,063,043 A | * | 11/1998 | Meyer et al. | 600/586 |

* cited by examiner

*Primary Examiner*—Francis Jaworski
(74) *Attorney, Agent, or Firm*—Jensen & Puntigam, P.S.

(57) ABSTRACT

The system includes an ultrasound apparatus which provides successive images of a bladder during the voiding process, the images being approximately one second long so as to provide an accurate picture of the action of the bladder during voiding. The images are then processed to form a substantially continuous moving image, i.e. a video or motion picture. The video covers approximately five minutes so as to capture the entire voiding event. The system is initiated typically by the user by pressing a button or other implement on the ultrasound apparatus which is carried by a belt or on a garment adjacent the abdomen of the user. Several processing techniques are used to compensate for any movement of the user or the device during the voiding process so as to provide a coherent and continuous moving image of the bladder during the voiding process.

15 Claims, 2 Drawing Sheets

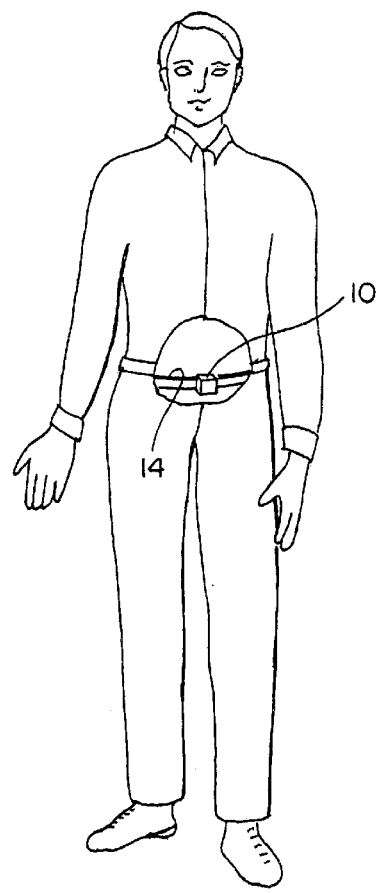
FIG.1
FIG.2
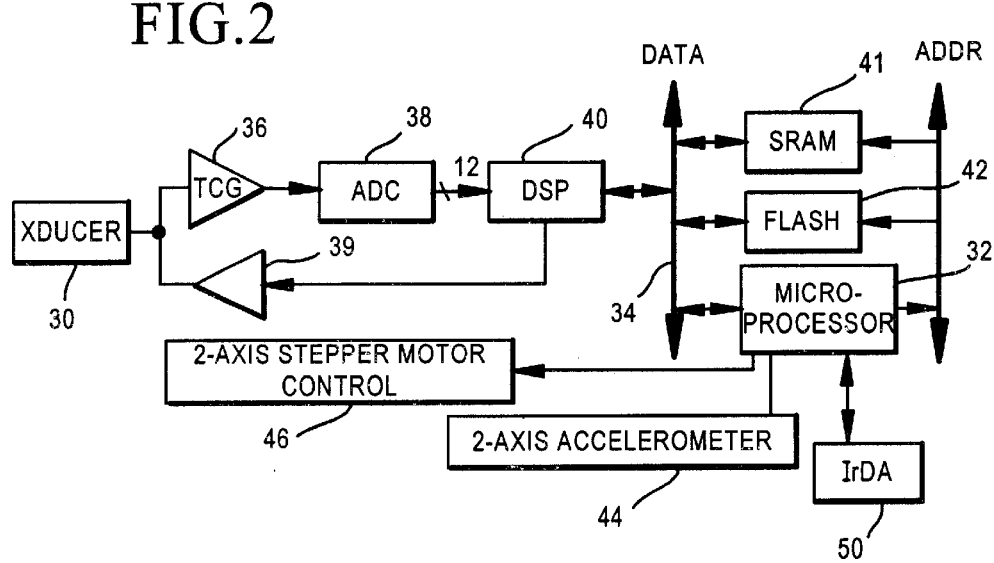

SYSTEM FOR IMAGING THE BLADDER DURING VOIDING

TECHNICAL FIELD

This invention relates generally to the art of medical ultrasound devices, and more specifically concerns the ultrasound imaging of the bladder.

BACKGROUND OF THE INVENTION

A critical function of the human bladder is the elimination of urine from the bladder at various times, referred to generally as voiding. Dysfunctions of the bladder involving the voiding process include an inability to completely empty the bladder, as well as various forms of incontinence, such as stress incontinence, stress urge overflow and nocturnal incontinence. Various clinical tests have been developed and used to diagnose specific bladder dysfunction. One commonly used test involves the measurement of the volume of urine that exits from the urethra using what is known as a uroflow machine. A "pulsing" flow as opposed to a smooth rise and then fall in flow volume is a possible indication of bladder muscles which are not contracting appropriately. The uroflow machine, however, provides only an indirect indication of actual bladder function. The uroflow machine is unable, for instance, to distinguish between bladder dysfunction, i.e. incorrectly operating bladder muscles, and sphincter muscle dysfunction.

In contrast, the action of the bladder itself can be seen during the voiding process by using videofluoroscopy. X-rays illuminate the internal bladder, with the resulting image being cast on a fluorescent screen. Cystourethrography is another technique which uses X-rays to produce images of the bladder and urethra during voiding. The contrast of the various portions of the urinary system relative to surrounding tissue can be enhanced by various isotope-type drinks taken prior to the procedure. However, such X-ray type equipment is expensive and is sufficiently large that natural voiding is difficult. Also, the use of such equipment inherently involves potentially hazardous X-rays.

Ultrasound devices have been used in the past for diagnosis of various medical conditions, and are generally regarded as being both safe and effective. However, conventional ultrasound machines produce only two-dimensional images and are large enough to effectively prevent natural voiding. The ability of an apparatus to permit a patient to void in a natural manner is quite important for accurate diagnosis of actual bladder function, since the manner in which the patient voids can significantly affect the physical action of the bladder. In some postures, such as required by particular equipment, a patient may exercise more abdominal pressure than would be optimal for correct bladder function. On the other hand, if the patient must be supine, as would be the case for procedures using X-ray machines, the patient may apply less than optimal abdominal pressure, which could also produce inaccurate results.

Hence, it is desirable to have an apparatus which can be placed on the user which would not interfere with normal voiding action, yet be capable of producing accurate images of the actual bladder during the voiding process.

DISCLOSURE OF THE INVENTION

The present invention includes a system and method for continuously imaging a human bladder during voiding, comprising: generating successive images of a bladder during voiding, the images being sufficiently close in time to provide a sequence of images showing the bladder during voiding; controlling the operation of the ultrasound apparatus so that images of the bladder during voiding are captured; and processing said images to form a substantially continuous moving image, in the nature of a motion picture, during voiding, so that the functioning of the bladder during voiding can be directly observed.

BRIEF DESCRIPTION OF THE DRAWINGS

FIG. 1 is a simplified diagram showing the device of the present invention in place on a patient.

FIG. 2 is a block diagram of the system of the present invention.

BEST MODE FOR CARRYING OUT THE INVENTION

Figure 4:
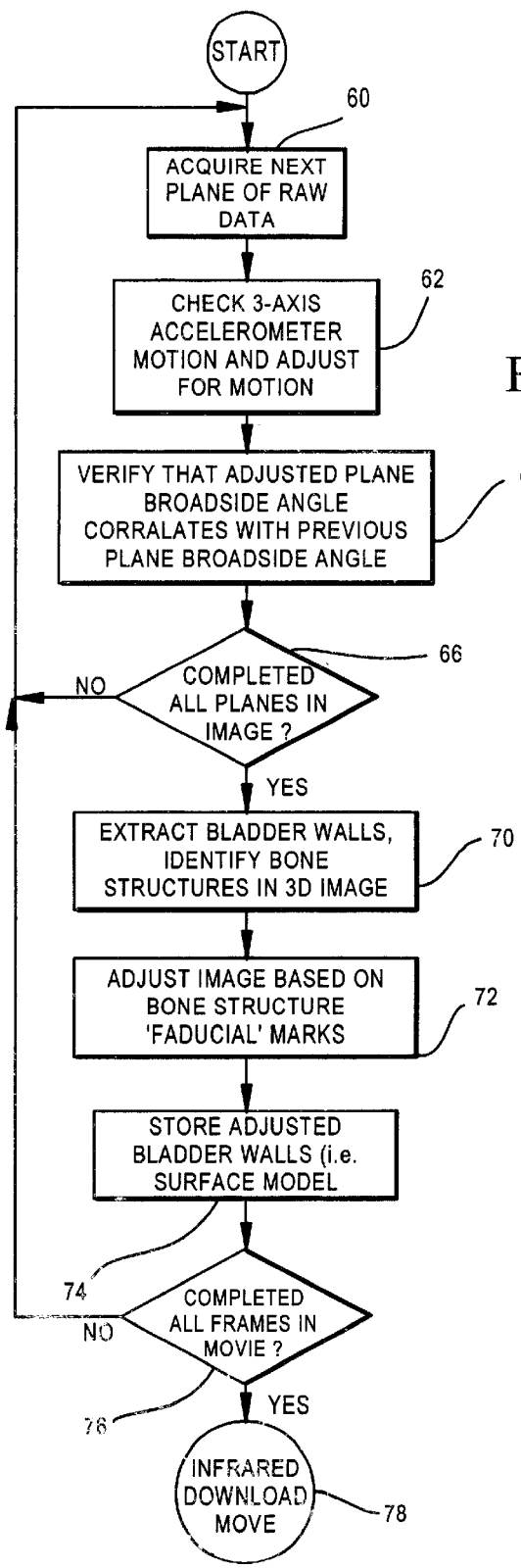
FIG. 4 is a software flowchart for the control sequence of the present invention.

Referring to FIG. 1, the system of the present invention includes an ultrasound device, shown generally at 10, which uses an ultrasound pulse generating and processing system to sample a three-dimensional solid angle scan cone volume also referred to as an image cone volume. In general, the ultrasound device is positioned on the body of a patient so that the patient's bladder is encompassed within the scan cone volume.

The ultrasound device 10 includes a microprocessor and is powered by a conventional battery. In operation, the ultrasound device produces a series of ultrasound signals, referred to as scan lines, each scan line spatially sampling a line segment of the image cone volume. The totality of scan lines completely samples the image cone and defines the boundaries of the image cone. The relative physical arrangement of the ultrasound device 10 and the scan cone 12 which is sampled by the scan lines, relative to selected body elements, in particular pubis bone 18, bladder 20 and spine 22, is shown in FIG. 3.

As indicated above, the ultrasound device 10 is designed and controlled in operation to sample a three-dimensional image cone volume which includes the patient's bladder. The ultrasound device 10 is dimensionally quite small and relatively light, having dimensions approximately 6 cm by 3 cm by 9 cm, weighing approximately 150 grams, and is held in place by a belt or similar device 14. Ultrasound device 10 can also be positioned against a patient's abdomen as part of a garment or the like. Such arrangements result in the patient being able to void in a natural manner, substantially unobstructed by the apparatus.

A conventional gel pad (not shown) can be used to properly "couple" the ultrasound device 10 to the patient. The gel pad in addition provides some mechanical connection capability between the device 10 and the patient.

Figure 3:
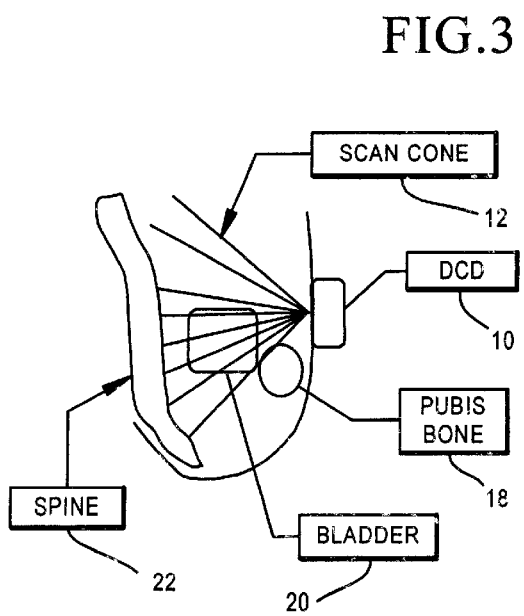
FIG. 3 is a diagram showing the internal body coverage by the ultrasound scanning system of the present invention.

In the particular arrangement of the present invention, the operation of the device is controlled so as to produce a series of 24 B-mode scan line ultrasound signals to fully image the bladder, each scan line covering approximately 120° in a single plane, as shown in FIG. 3. Successive scan lines are separated in the embodiment shown by approximately 7.5° in a plane orthogonal to the scan line plane. The set of 24 scan lines, each covering 120°, provides what is referred to as the ultrasound interrogation signal.

Such a system for producing an ultrasound interrogation signal, transmitting the signal to cover a defined scan cone, receiving the returning signal, and then processing the return signal to produce a three-dimensional view of the bladder, is known. Examples of two approaches which can be used to produce three-dimensional images, one using a single transducer which is moved in a controlled manner, and the other using multiple fixed transducers arranged in a particular pattern, are shown in U.S. Pat. No. 4,926,871 to Ganguly et al, and U.S. Pat. No. 5,235,985 to McMorrow et al, respectively, both of which are owned or exclusively licensed by the assignee of the present invention. Both of those patents are hereby incorporated by reference.

The '871 and '985 patents provide detailed explanations of the generation, transmission and return of ultrasound signals relative to a bladder. The '985 patent teaches the calculation of a three-dimensional bladder image from the received ultrasound signals. Accordingly, a detailed explanation of the ultrasound apparatus and the particular processing of the received signals to produce an individual three-dimensional image is not included herewith.

The three-dimensional scan cone within which the bladder is located can be interrogated (data collection), the bladder walls identified (data processing), and the three-dimensional image constructed, in approximately one second using conventional ultrasound principles. In the system of the present invention, such a single image is treated as one frame in a complete sequence of frames, which is referred to herein as a bladder movie or video. In the system of the present invention, approximately 300 successive frames are arranged into a five minute video. The video is produced and then stored, following initiation of the data collection sequence. Typically, five minutes is sufficient time for a patient to begin and complete the urinating event, so that the entire voiding sequence of the bladder is captured in a single motion picture video.

The resulting ultrasound video, showing the bladder in three dimensions, in essence captures the movement and action of the bladder during the entire voiding sequence, i.e. the video shows the bladder as it changes shape and contracts as well as the action of the muscles and the bladder itself during the entire voiding process. This is valuable information to the health professional, enabling him or her to directly observe the bladder muscle movement and contraction during voiding, so as to make accurate diagnostic determinations relative to the condition of the bladder and to separate bladder malfunction from malfunction of other parts of the urological system.

The system of the present invention has a number of specific characteristics which ensure an accurate video representation of bladder action. One important issue relative to the production of the bladder video is frame-to-frame correlation. The patient may either move considerably during the time period of the video or the ultrasound device itself may move on the body, which results in motion in the video image. This is undesirable, and there are a number of features which can be used to compensate for this motion.

The first feature is a cross-correlation analysis relative to the common scan line for each successive scan plane. Successive ultrasound scan planes result in successive frames in the video, following processing of the returned ultrasound signals in the scan plane. As indicated above, in the embodiment shown, 24 B-mode 120° scan lines complete the scanning of the cone. Each successive scan line is rotated 7.5° around a common broad-side scan line relative to the previous scan line. The time interval between successive scan lines is quite small compared to the possible time interval of motion of the patient or the ultrasound device.

Since the broad-side scan line is common to each of the successive scan lines, any difference in the digitized return signal is most likely due to motion, as opposed to a significant change in the patient's internal anatomy. In cross correlation analysis, if the most recent scan line does not sufficiently correlate with the previous scan line, that particular scan line (the most recent one) is run again.

In the correlation calculation, each element in the digitized received back-scatter is multiplied with the same element in the previous digitized received back-scatter. A total correlation figure of merit of the two systems is then obtained by summing all of the individual multiples (one for each element in the digitized return). If the two digitized arrays are similar then the multiplication tends to reinforce and a larger correlation value is obtained.

In another compensation technique, conventional three-dimensional microaccelerometers are used. Such accelerometers are commercially available from Analog Devices and other manufacturers. The accelerometers constantly track the motion of the ultrasound device as the ultrasound scanning is being performed. In the accelerometers, standard chips have miniature beams monolithically etched to be 90° apart. Accordingly, this results in any motion in the X–Y plane being detected. Two such chips are used, one located in the X–Y plane, and the other mounted orthogonally in the X–Z plane. A data collection device (DCD) moves freely in space, for detection of motion of the ultrasound device on the patient.

The patient is assumed to be relatively motionless.

Still further, absolute reference points are used inside the body to continuously locate the ultrasound device. The ultrasound device automatically recognizes and locates the bones of the pelvis, in particular the pubic bone and the lower spinal column. These bones can be identified because they have a significantly different acoustic impedance than tissue. In fact, they appear to be empty areas in the ultrasound images. The bladder is non-echogenic because the ultrasound signals travel through urine unimpeded, while bones are non-echogenic because very little ultrasound can penetrate bone. Each three-dimensional video frame processed from the returning ultrasound signal is oriented so the absolute reference points remain stationary throughout the entire video sequence, on a frame-to-frame basis. The abdominal skeletal anatomy thus is used as identification "marks" to keep the image cone located in one spot throughout the imaging process.

FIG. 3 shows a simplified block diagram of the system of the present invention. The ultrasound transducer 30, which is conventional, in response to a command from microprocessor 32, through data bus 34, digital signal processor (DSP) 40 and amplifier 39 produces a first 120° scan line ultrasound signal. The signal is transmitted in the direction of the bladder as shown in FIG. 3 and is returned to transducer 30 as received (returned) back-scatter information.

The return information is then applied to a time-controlled gate amplifier (TCG) 36, the output of which is applied to a conventional analog-to-digital converter 38. The time-controlled gate amplifier 36 is conventional in ultrasound applications. The amplifier increases in gain the deeper into a particular bodily region the ultrasound is to reach.

The output of the analog-to-digital converter 38 is a digital signal, on 12 output lines. The digital signal is then applied to the conventional digital signal processor 40 which processes the received back scatter ultrasound information. Each scan line is processed successively and transferred to RAM memory 41. The return ultrasound signal is processed by a program stored in flash memory 42. The information from the two-axis accelerometers 44 is applied to microprocessor 32. Microprocessor 32 also performs the cross-correlation analysis on each successive scan line of returned data, in the manner disclosed above. Microprocessor 32 then moves the two-axis stepper motor 46 on which transducer 30 is mounted to the correct position for the next scan line if the previous scan line has passed the cross-correlation test. This process continues until one complete scan sequence has been accomplished.

Typically, as indicated above, each complete scan of the bladder and the processing necessary to produce a three-dimensional image therefrom takes about one second and comprises one frame of the final bladder video. The five-minute complete video is then transferred to a personal computer (not shown) through an IRDA (infrared) serial data port 50. The personal computer is then used to view the bladder video. Typically, the program capability of the personal computer will include various 3-D motion picture (video) display tools. For instance, the video may be played at real time or at varying speeds, faster or slower than real time. A "filling" phase for the bladder, for instance, can be displayed at an accelerated speed, while the voiding phase may be played at real time or even slower. The digital video file can also be transferred over the internet to a web data base server.

The software flow-chart for the system is shown in FIG. 4. At the start of the program sequence, one plane of raw data is obtained by the ultrasound system, as shown at block 60. In the next step, accelerometer motion, if any, is checked at block 62 and any adjustment of the data relative to detected motion of the ultrasound device is made. Following the accelerometer check, the adjusted broad-side angle is reviewed to determine if it correlates with the previous scan plane broad-side angle, as shown at block 64. This continues until all the planes for a single complete image of the bladder have been completed, as shown at block 66. If all the planes have not been completed, the steps of blocks 60, 62 and 64 are repeated until, all 24 scan planes have been processed.

At this point, the returned ultrasound information is processed to determine the location of the bladder walls as well as identifying the fixed bone structures in the image, as shown at block 70. The image is then adjusted, if necessary, to ensure that the selected bone structures are in the same place in each successive image frame. Each three-dimensional image is then stored as a single frame, as shown at block 74. This process continues until all of the frames for the video (300 for a five-minute video) have been completed, as shown at block 76. Once this has been done, the resulting video is downloaded, via the infrared or other port, as shown at block 78. The video can be transferred over the internet for remote storage and viewing.

As indicated above, if the patient can void upon command, he/she can initiate the ultrasound video process. The next five minutes after such initiation is the time span covered by the bladder video in the embodiment shown. The time span could differ. Alternatively, the patient could suffer some degree of incontinence, and thus void unpredictably. This can occur under various circumstances. In such a circumstance, there is no timely initiation of the video recording by the patient. One solution is that, with sufficient battery life, the bladder can be scanned at a one Hertz rate with simply the most recent five minutes being saved, by continuously overriding the video memory. In such a situation, the volume of the bladder is continuously monitored. When a significant drop in bladder volume is noted, the continuous overriding of the video memory is terminated, assuming that the significant drop in volume is an indication of the end of the voiding episode. The video tape thus has the most recent five minutes captured. Battery life can be prolonged if a scan is made at a lower rate (lower than one Hertz), with an increase in scan speed as soon as any drop in volume is detected.

Alternatively, the image can be saved based on a percentage change in volume and by recording the time of the image saved. In such an arrangement, the memory is used efficiently to record more sample points the more the volume changes. The scanning rate can also be dynamically changed using this approach. In effect, the time between scans can be shortened the more the volume is actually changing, resulting in more efficient use of battery and memory.

Accordingly, the present invention is directed toward a system for providing an ultrasound video of the actual action of the bladder during a voiding event. The video sequence comprises a series of ultrasound images at approximately one frame per second. Various techniques are used to ensure a stable continuous image over the duration of the video. The video may be initiated by the patient, or through an automatic scanning technique.

Although a preferred embodiment of the invention has been disclosed here for purposes of illustration, it should be understood that various changes, modifications and substitutions may be incorporated without departing from the spirit of the invention, which is defined by the claims which follow.

What is claimed is:

1. A system for imaging a human bladder during voiding, comprising:
   an ultrasound apparatus attachable to a patient for generating successive images of a bladder during voiding, the images being sufficiently close in time to provide a sequence of images showing the bladder during voiding;
   means controlling operation of the ultrasound apparatus so that images of the bladder during voiding are captured; and
   a processor for processing said images to form a substantially continuous moving image of the bladder during voiding, so that actual functioning of the bladder during voiding can be directly observed.

2. A system of claim 1, said processor including a system for compensating for motion artifacts during the voiding process.

3. A system of claim 2, wherein the motion artifact is motion by the patient.

4. A system of claim 2, wherein the motion artifact is motion by the ultrasound apparatus relative to the patient.

5. A system of claim 2, including means for performing a cross-correlation analysis between successive scan planes in the generation of each successive video image.

6. A system of claim 2, including a three-axis accelerometer which tracks the motion of the ultrasound apparatus.

7. A system of claim 2, said processor including processing means using bone portions within the patient as reference points for image-to-image correlation.

8. A system of claim 1, wherein the ultrasound apparatus is adopted to be initiated by the patient prior to the start of voiding.

9. A system of claim 1, wherein the controlling means is operative such that the bladder is automatically scanned at selected intervals and wherein the generation of the continuous moving image is terminated when a significant drop in volume of the bladder is detected, the system including means for saving the continuous image covering a selected interval of time immediately prior to the significant drop in volume.

10. A system of claim 1, wherein the substantially continuous image covers approximately five minutes.

11. A system of claim 1, including means for transmitting the continuous moving image over the internet to a remote location.

12. A method for imaging a human bladder during voiding, comprising:

generating successive images of a bladder during voiding by an ultrasound apparatus attachable to a patient, the images being sufficiently close in time to provide a sequence of images showing the bladder during voiding;

controlling operation of the ultrasound apparatus so that images of the bladder during voiding are captured; and processing said images to form a substantially continuous moving image of the bladder during voiding, so that actual functioning of the bladder during voiding can be directly observed.

13. A method of claim 12, including the step of compensating for motion artifacts during the voiding process.

14. A method of claim 12, including the step of using bone portions within the patient as reference points for image-to-image correlation.

15. A method of claim 12, including the step of transmitting the continuous moving image over the internet to a remote location.

* * * * *